United States Patent [19]

Lunn

[11] 4,396,620
[45] Aug. 2, 1983

[54] CEPHALOSPORIN QUINOLINIUM BETAINES

[75] Inventor: William H. W. Lunn, Indianapolis, Ind.

[73] Assignee: Eli Lilly and Company, Indianapolis, Ind.

[21] Appl. No.: 300,131

[22] Filed: Sep. 8, 1981

[51] Int. Cl.$^3$ .................. A61K 31/545; C07D 501/46
[52] U.S. Cl. ...................................... 424/246; 544/22
[58] Field of Search ........................ 544/22; 424/246

[56] References Cited

U.S. PATENT DOCUMENTS

| | | | |
|---|---|---|---|
| 4,098,888 | 7/1978 | Ochiai et al. | 424/246 |
| 4,152,432 | 5/1979 | Heymes et al. | 424/246 |
| 4,160,830 | 7/1979 | Morimoto et al. | 424/246 |
| 4,200,575 | 4/1980 | Numata et al. | 424/246 |
| 4,260,747 | 4/1981 | Heymes et al. | 544/27 |
| 4,264,595 | 4/1981 | Numata et al. | 424/246 |
| 4,278,793 | 7/1981 | Durckheimer et al. | 544/28 |

*Primary Examiner*—Paul M. Coughlan, Jr.
*Attorney, Agent, or Firm*—William B. Scanlon; Arthur R. Whale

[57] ABSTRACT

Broad spectrum cephalosporin antibiotics represented by the formula

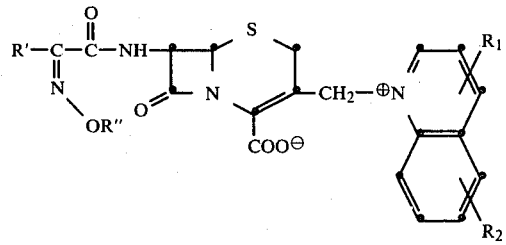

wherein R' is a heterocyclic, eg. 2-aminothizol-4-yl or 5-amino-1,2,4-thiadiazol-3-yl; R'' is $C_1$–$C_4$ alkyl, a carboxy-substituted alkyl or cycloalkyl group, or an N-substituted carbamoyl group; and $R_1$ and $R_2$ represent substituent groups, eg. amino, hydroxy, halogen, carboxy, carbamoyl, alkyl, alkylamino, sulfo, and sulfonamido; and formulations of the antibiotics are provided. The antibiotics are useful in a method for treating bacterial infections.

19 Claims, No Drawings

CEPHALOSPORIN QUINOLINIUM BETAINES

BACKGROUND OF THE INVENTION

This invention relates to semi-synthetic cephalosporin antibiotic compounds. In particular, it relates to cephalosporin compounds wherein the cephalosporin bicyclic nucleus is substituted in the 3'-position with a substituted quinolinium group and in the 7-position with a 2-heterocyclic-2-oximinoacetamido group.

Cephalosporin compounds substituted in the 3'-position with a quaternary ammonium group have been known for some time. For example, cephalosporin CA (pyridine) was one of the first derivatives of cephalosporin C prepared by Abraham et al. following the discovery of cephalosporin C, Hale, Newton, and Abraham, *Biochem. J.*, 79, 403 (1961).

Cephaloridine, the well-known clinical antibiotic, is the 3'-pyridinium cephalosporin, 7-(α-thienylacetamido)-3-(pyridinium-1-ylmethyl)-3-cephem-4-carboxylate. Recently, Heymes et al., U.S. Pat. No. 4,152,432, described semi-synthetic cephalosporin antibiotics wherein the 7-position side chain is a 7-[2-(2-(aminothiazol-4-yl)-2-alkoxyiminoacetamido] group and the 3-position substituent is acetoxymethyl. More recently, O'Callaghan, et al., in U.S. Pat. No. 4,258,041, describe 7-[2-(2-aminothiazole-4-yl)-2-oximinoacetamido]-3-(pyridinium-1-ylmethyl)-3-cephem-4-carboxylate antibiotics, and the corresponding compounds wherein the pyridinium group in the 3'-position is substituted with a carbamoyl group.

Because of the continuing need for improved antibiotic therapy in clinical practice, the search continues for broad spectrum antibiotics with greater potency and minimal toxicity. The semi-synthetic cephalosporin antibiotics long have been recognized as broad spectrum antibiotics, and several have achieved clinical importance. Continued research with the cephalosporin antibiotics has centered of late on the development of antibiotics having higher activity against certain gram-negative microorganisms such as pseudomonas and those which produce β-lactamase destructive of β-lactam antibiotics.

SUMMARY

Broad spectrum cephalosporin antibiotics represented by the following structural formula are provided by this invention.

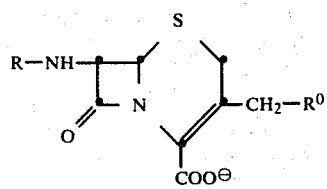

In the above formula R is hydrogen or a 2-(heterocyclic)-2-oximinoacetyl group and $R^0$ represents a substituted quinolinium group. For example 7-[2-(2-aminothiazol-4-yl)-2-methoxyiminoacetamido]-3-(4-aminoquinolinium-1-ylmethyl)-3-cephem-4-carboxylate is a highly active antibiotic useful for combatting infections caused by gram-negative and gram-positive microorganisms pathogenic to man and animals.

The compounds of the invention are preferably prepared by the reaction of a 3-iodomethyl cephalosporin having the 7-position acyl side chain of the compounds of the invention with a substituted quinoline.

Pharmaceutical compositions comprising a compound of the invention are provided as well as a method for the treatment of infectious diseases.

DETAILED DESCRIPTION

The antibiotic compounds of the invention are represented by the following formula 1.

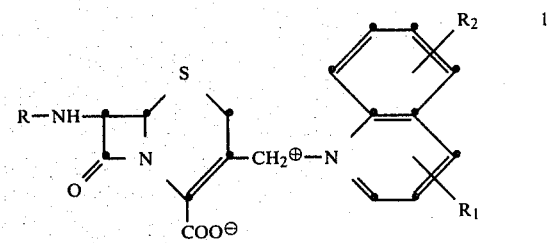

wherein R is hydrogen, formyl, or an acyl group represented by the formula

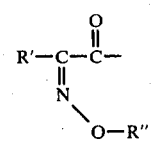

wherein R' is a 5- or 6-membered heterocyclic ring represented by the formulas

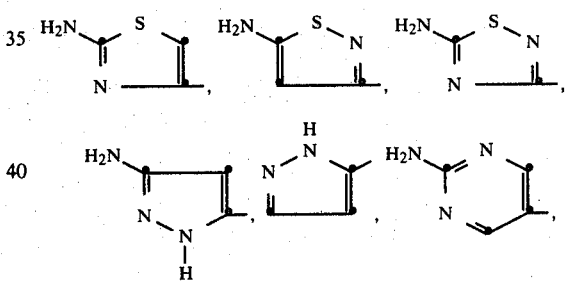

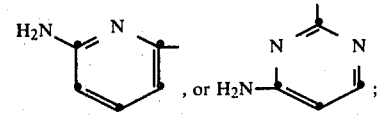

R" is hydrogen, $C_1$–$C_4$ alkyl, a carboxy-substituted alkyl or carboxy-substituted cycloalkyl group represented by the formula

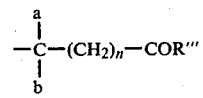

wherein n is 0–3, a and b when taken separately are independently hydrogen or $C_1$–$C_3$ alkyl, or when taken together with the carbon to which they are attached form a $C_3$–$C_7$ carbocyclic ring; R''' is hydroxy, $C_1$–$C_4$ alkoxy, amino, and when R''' is hydroxy a carboxy-protecting group;

or R" is a carbamoyl group represented by the formula

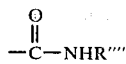

wherein R'''' is $C_1$-$C_4$ alkyl, phenyl, or $C_1$-$C_3$ alkyl substituted by phenyl;

$R_1$ and $R_2$ independently are hydrogen, amino, $C_1$-$C_4$alkylamino, di-($C_1$-$C_4$)alkylamino, hydroxy, $C_1$-$C_4$alkoxy, halogen, $C_1$-$C_4$ alkyl, cyano, trifluoromethyl, sulfo(—$SO_3H$), aminosulfonyl (—$SO_2NH_2$), carboxy, $C_1$-$C_4$ alkoxycarbonyl, carbamoyl, thiocarbamoyl, hydroxy-substituted $C_1$-$C_3$alkyl, formyl, or $C_2$-$C_4$alkanoyl; provided that one of $R_1$ and $R_2$ is other than hydrogen; and the pharmaceutically acceptable non-toxic salts thereof.

In the above formula 1 the term, $C_1$-$C_4$ alkyl, refers to methyl, ethyl, n-propyl, iso-propyl, n-butyl, sec-butyl, and like lower alkyl radicals; $C_1$-$C_3$ alkyl substituted by phenyl, refers to benzyl, 2-phenethyl, 3-phenylpropyl, 2-phenylpropyl and the like; $C_1$-$C_4$alkylamino refers to methylamino, ethylamino, n-propylamino, n-butylamino, iso-propylamino, and like mono lower alkyl amino groups; di($C_1$-$C_4$alkyl) amino refers to dimethylamino, diethylamino, methylethylamino, di(n-butyl)amino, di-(n-propyl)amino, and the like; $C_1$-$C_4$ alkoxy refers to methoxy, ethoxy, n-propoxy, iso-propoxy, n-butoxy, t-butoxy, and the like; $C_1$-$C_4$ alkoxycarbonyl refers to methoxycarbonyl, ethoxycarbonyl, isopropoxycarbonyl, t-butoxycarbonyl, and the like; and examples of $C_2$-$C_4$alkanoyl groups, include acetyl, propionyl, butyryl, and the like.

Examples of carbamoyl groups represented by R'' in the formula 1 are N-methylcarbamoyl, N-ethylcarbamoyl, N-phenylcarbamoyl, N-benzylcarbamoyl, and N-(2-phenylethyl)carbamoyl.

Examples of carboxy-substituted alkyl and cycloalkyl groups represented by R''' in formula 1 wherein R''' is hydroxy are carboxymethyl, 2-carboxyethyl, 3-carboxypropyl, 2-carboxyprop-2-yl, 2-carboxyprop-1-yl, 1-carboxyethyl, 1-carboxycycloprop-1-yl, 1-carboxycyclobut-1-yl, 1-carboxycyclopent-1-yl, 1-carboxycyclohex-1-yl, 1-carboxymethylcyclobut-1-yl, 1-(3-carboxypropyl)cyclopent-1-yl, and the like; and when R''' is amino, examples of such carboxamido-substituted alkyl and cycloalkyl groups are the primary amides of the carboxy-substituted alkyl and carboxy-substituted cycloalkyl groups named above.

Examples of $C_1$-$C_4$ alkyl esters of the carboxy-substituted alkyl and cycloalkyl groups represented when R''' is $C_1$-$C_4$ alkoxy are methoxycarbonylmethyl, ethoxycarbonylmethyl, isopropoxycarbonylmethyl, ethoxycarbonylethyl, 2-ethoxycarbonylprop-2-yl, 1-methoxycarbonylcyclobut-1-yl, 1-methoxycarbonylmethylcyclopent-1-yl, 1-ethoxycarbonylcyclohex-1-yl, and like alkyl and cycloalkyl esters.

When R''' in the formula 1 is a carboxy-protecting group, the compounds represented are esters of the compounds wherein R''' is hydroxy. Such carboxy-protecting ester groups include those readily removable ester groups commonly used in the β-lactam art for the temporary protection of the carboxy group. Examples of such R''' groups are t-butyloxy, 2,2,2-trichloroethoxy, 2-iodomethoxy, benzyloxy, diphenylmethoxy, p-nitrobenzyloxy, p-methoxybenzyloxy, and trialkylsilyloxy groups such as trimethylsilyloxy, and like groups.

The substituted quinolinium group in the 3'-position of the compounds of the invention (formula 1) is exemplified by the following: amino-substituted quinolinium groups such as 3-aminoquinolinium, 4-aminoquinolinium, 5-aminoquinolinium, 3,6-diaminoquinolinium, 4-amino-8-methylquinolinium, 3-methoxy-5-aminoquinolinium, 3-amino-7-cyanoquinolinium, 4-amino-6-acetylquinolinium, 5-amino-8-sulfoquinolinium, 4-amino-5-trifluoromethylquinolinium, 3-chloro-5-aminoquinolinium, and the like; $C_1$-$C_4$ alkyl and di($C_1$-$C_4$alkyl)amino-substituted quinolinium groups such as 3-methylaminoquinolinium, 3-dimethylaminoquinolinium, 5-diethylaminoquinolinium, 3-ethyl-5-ethylaminoquinolinium, 3-ethyl-5-di(n-propyl)aminoquinolinium, 6-chloro-3-n-butylaminoquinolinium, 6-bromo-4-dimethylaminoquinolinium, and the like; hydroxy-substituted quinolinium groups such as 3-hydroxyquinolinium, 5-hydroxyquinolinium, 3-hydroxy-5-cyanoquinolinium, 4-hydroxy-6-aminoquinolinium, 3-methyl-5-hydroxyquinolinium, 4-carbamoyl-8-hydroxyquinolinium, and the like; $C_1$-$C_4$ alkoxy-substituted quinolinium groups such as 3-methoxyquinolinium, 8-ethoxyquinolinium, 7-isopropoxyquinolinium, 3-chloro-5-methoxyquinolinium, and the like; haloquinolinium groups such as 4-chloroquinolinium, 3-methyl-4-chloroquinolinium, 5-bromoquinolinium, 3,7-dichloroquinolinium, 3-hydroxy-5-chloroquinolinium, 3-cyano-5-bromoquinolinium, 4-carbamoyl-5-chloroquinolinium, and the like; cyanoquinolinium groups such as 3-cyanoquinolinium, 3-ethyl-6-cyanoquinolinium, 4-chloro-6-cyanoquinolinium, 5-cyanoquinolinium, 3-chloro-5-cyanoquinolinium, 3-amino-5-cyanoquinolinium, and the like; trifluoromethyl and alkyl-substituted quinolinium groups such as 3-trifluoromethylquinolinium, 5-trifluoromethylquinolinium, 8-trifluoromethylquinolinium, 3-methyl-4-trifluoromethylquinolinium, 4-chloro-6-trifluoromethylquinolinium, 4-cyano-6-trifluoromethylquinolinium, 3-carboxy-5-trifluoromethylquinolinium 4-t-butylquinolinium, 3-methylquinolinium, 6-n-propylquinolinium, and the like; formyl and $C_2$-$C_4$ alkanoyl substituted quinolinium groups such as 3-formylquinolinium, 3-acetylquinolinium, 4-formylquinolinium, 4-formyl-6-chloroquinolinium, 3-methoxy-6-acetylquinolinium, 5-butyrylquinolinium, 8-cyano-5-acetylquinolinium, and the like; carbamoyl and thiocarbamoyl-substituted quinolinium groups such as 4-carbamoylquinolinium, 4-thiocarbamoylquinolinium, 5-carbamoylquinolinium, 3-carbamoyl-5-hydroxyquinolinium, 8-chloro-4-carbamoylquinolinium, 3-trifluoromethyl-5-carbamoylquinolinium, 3-methyl-5-thiocarbamoylquinolinium, 6-carbamoyl-3-ethylquinolinium, and the like; and sulfo, sulfonamido, hydroxy-$C_1$-$C_3$ alkyl, and carboxy-substituted quinolinium groups such as 5-sulfoquinolinium, 4-sulfoquinolinium, 3-hydroxymethylquinolinium, 4-sulfonamidoquinolinium, 3-methyl-5-sulfoquinolinium, 4-carboxyquinolinium, 6-carboxyquinolinium, 4-chloro-6-carboxyquinolinium, 3-acetyl-5-carboxyquinolinium, 6-fluoro-3-sulfonamidoquinolinium, 6-(2-hydroxyethyl)-3-methylquinolinium, and like mono- and di-substituted quinolinium groups.

The compounds of the invention wherein R in formula 1 is an acyl group of the formula

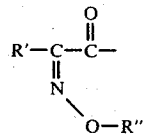

and R' is 2-aminothiazol-4-yl, 5-aminoisothiazol-3-yl, 5-amino-1,2,4-thiadiazol-3-yl, 3-aminopyrazol-5-yl, pyrazol-5-yl, 3-aminopyrimidin-5-yl, 4-aminopyrimidin-2-yl, or 2-aminopyridin-6-yl, inhibit the growth of microorganisms pathogenic to man and animals. These compounds are broad spectrum antibiotics which are useful in the treatment of infectious diseases.

The term "oximino" is used herein for convenience in designating the oxime and substituted oximes represented by the group

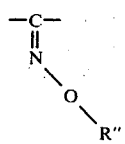

in the formula 1.

The compounds of the formula 1 wherein R is hydrogen or formyl are useful intermediates which can be used in the preparation of the 7-acyl compounds of formula 1 as described hereinafter.

The compounds of the formula 1 wherein R is an acyl group as defined can be prepared by alternative methods. According to a preferred method for preparing the 7-acyl compounds a 7-acylamino-3-acetoxymethyl cephalosporin, wherein the 7-acyl group is as defined for the formula 1, is converted to a 3-halomethyl derivative and the 3-halomethyl derivative is reacted with a substituted quinoline to obtain a compound of the invention. The method of preparation is illustrated by the following reaction scheme.

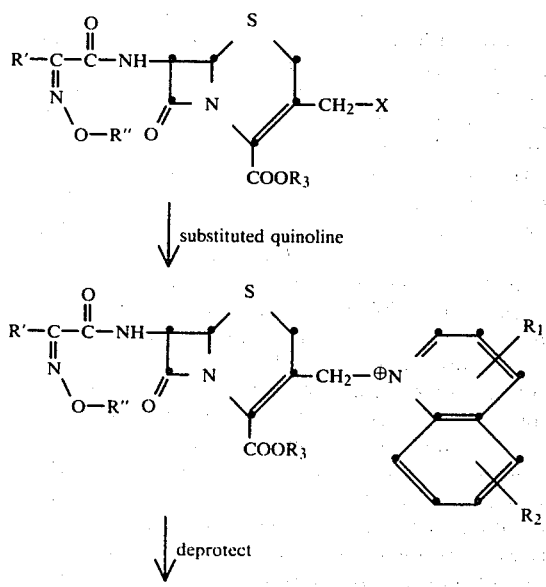

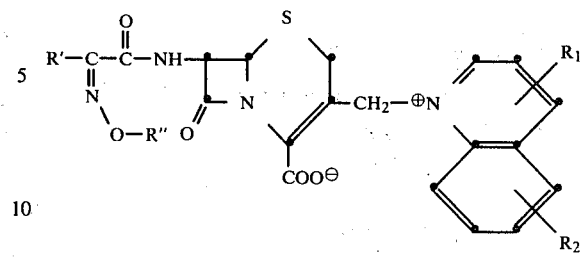

In the above formulas, R', R", $R^1$ and $R^2$ have the same meanings as defined hereinabove, X is chloro, bromo, or iodo, and $R_3$ is a carboxy-protecting group. The amino group of the amino-substituted heterocyclic R' also may be protected during the reaction and is desirably protected during the preparation of the 3-halomethyl derivative. The amino-protecting group can be a conventional protecting group such as trityl, an alkoxycarbonyl or aryloxycarbonyl group eg., t-butyloxycarbonyl, t-amyloxycarbonyl, 2,2,2-trichloroethoxycarbonyl, benzyloxycarbonyl, p-nitrobenzyloxycarbonyl, or like protecting group; or a trialkylsilyl protecting group such as trimethylsilyl. The carboxy-protecting group, $R_3$, can be a readily removable ester group, such as is described hereinabove for the term R'''. Preferably $R_3$ is a trialkylsilyl group eg., trimethylsilyl.

The preferred method for preparing the compounds of the invention comprises the use of a 7-acylamino-3-iodomethyl derivative wherein the carboxy and amino groups are protected by silylation such as with a lower trialkylsilyl group, preferably trimethylsilyl. In carrying out the preparation of a compound of the invention by the preferred method, the 7-acylamino-3-acetoxymethyl-3-cephem-4-carboxylic acid is first silylated to block the reactive carboxyl and amino functional groups present in the molecule. The silylation is carried out with one of the commonly employed silylating agents, for example, mono- or bis-trimethylsilylacetamide or, preferably, with N-trimethylsilyltrifluoroacetamide. The silylation is carried out in an inert solvent such as a halogenated hydrocarbon solvent, for example, methylene chloride, chloroform, chloroethane, or other inert organic solvent such as acetonitrile or propionitrile. The silylated derivative is then allowed to react with trimethylsilyliodide (TMSI) to form the corresponding 3-iodomethyl silylated derivative. The reaction mixture containing the silylated 3-iodomethyl derivative is evaporated to remove the solvent, and the concentrate is dissolved in acetonitrile and is treated with a slight excess of tetrahydrofuran to degrade any excess TMSI. To this solution is then added the substituted quinoline to form a compound of formula 1 as the silylated derivative. Upon the addition of water, the silyl derivative is hydrolyzed to form a compound of the invention.

The following reaction scheme illustrates the preparation of the compounds of the invention.

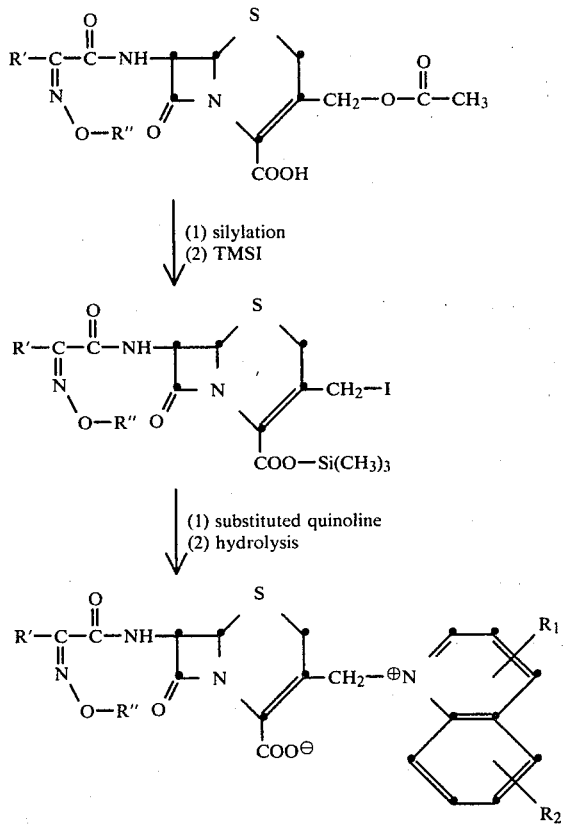

The preparation of the 3-iodomethylcephalosporin intermediate is carried out according to the process described by Bonjouklian in U.S. Pat. No. 4,266,049, issued May 8, 1981. In carrying out the preparation of the 3-iodomethylcephalosporin, other trialkylsilyl iodides may be employed as described by Bonjouklian. Trimethylsilyl iodide is the preferred reagent and is used to illustrate the preparation of the compounds herein.

In an example of the preparation of a compound of the invention, syn-7-[2-(2-aminothiazol-4-yl)-2-methoxyiminoacetamido]-3-acetoxymethyl-3-cephem-4-carboxylic acid is suspended in an inert organic solvent such as chloroform and is silylated by employing N-methyl-N-trimethylsilyltrifluoroacetamide. A complete solution is obtained upon silylation. To the solution is then added trimethylsilyl iodide in at least a stoichiometric amount and, preferably, 2 to 3 times the stoichiometric amount. The mixture is stirred to assure complete formation of the 3-iodomethyl derivative. The 3-iodomethyl derivative need not be isolated and, preferably, is used as the silylated derivative in the next step of the reaction. Accordingly, the reaction mixture containing the silylated 3-iodomethyl derivative is evaporated to remove volatiles, for example, solvent, and is then dissolved in acetonitrile. To the solution is added tetrahydrofuran and the solution is stirred for a short while. The treatment of the silylated 3-iodomethyl derivative solution with tetrahydrofuran degrades any excess TMSI. The degradation enhances the recovery and purity of the final product.

The solution of the silylated 3-iodomethyl derivative is then mixed with a solution of the substituted quinoline in a suitable solvent such as acetonitrile. The reaction occurs readily and most conveniently at room temperature with stirring. After the reaction is complete, water is added to the mixture to hydrolyze the silyl-blocking groups, for example, the silyl ester formed with the $C_4$ carboxylic acid function. Following the addition of the water to the reaction mixture, the product commonly precipitates and is separated by filtration, centrifugation, or other suitable means. The product is generally crude at this stage of its preparation and can be purified by high performance liquid chromatography by reversed-phase $C_{18}$ silica chromatography using a solvent system of acetonitrile/acetic acid/water containing approximately 2% acetic acid and between about 10% and about 20% of acetonitrile.

The compounds of the invention can be prepared alternatively by acylation of a compound of the formula 1 wherein R is hydrogen, a 7-amino-3-(substituted quinolinium-1-ylmethyl)-3-cephem-4-carboxylate. The 3'-quaternary ammonium substituted nucleus compounds are prepared by reacting 7-aminocephalosporanic acid or a silylated derivative thereof with a substituted quinoline. The substituted nucleus is then acylated with an oximino-substituted derivative of the desired amino-substituted heterocyclic acetic acid represented by the formula

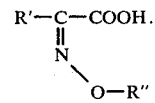

An active derivative of the oximino acetic acid is used in the acylation. For example, the acid group is reacted with hydroxybenzotriazole (HBT) and a carbodiimide such as dicyclohexylcarbodiimide, and the HBT ester used to acylate the 7-amino group of the nucleus. Other active derivatives such as the acid azide, the anhydride formed with methyl chloroformate or isobutyl chloroformate, can be used for acylation.

The compounds of the formula 1 wherein R is hydrogen also can be prepared by the N-deacylation of a 7-acylamino-3-(substituted quinolinium-1-ylmethyl)-3-cephem-4-carboxylate wherein the 7-acyl group is other than R' (formula 1). The 7-acyl group can be, for example, phenoxyacetyl, phenylacetyl, or 2-thienylacetyl. The N-deacylation is carried out by the well known procedure for the deacylation of cephalosporins and desacetoxycephalosporins in the preparation of 7-aminocephalosporanic acid and 7-aminodesacetoxycephalosporanic acid. According to the method, a 7-acylaminocephalosporin is reacted with an imino halide-forming reagent, such as phosphorus pentachloride or phosphorus trichloride in the presence of an acid-binding agent, to form the imino chloride of the 7-amido bond. The imino chloride is converted to the imino ether with an alcohol or glycol and the imino ether decomposes to the 7-amino nucleus compound.

In an example of the preparation of a 7-amino-3-(substituted quinolinium-1-ylmethyl)-3-cephem-4-carboxylate of this invention, 7-(2-thienylacetamido)cephalosphoranic acid is reacted with the substituted quinoline to form the 7-(2-thienylacetamido)-3-(substituted quinolinium-1-ylmethyl)-3-cephem-4-carboxylate. The latter is then converted to the trimethylsilyl ester on reaction in a halogenated hydrocarbon solvent such as methylene chloride or trichloroethane with trimethylchlorosilane in the presence of an amount of dimethylacetamide corresponding to a 4-5 molar excess. The solution of the silyl ester is cooled to a temperature of about −30° C. to about 0° C. and an imino halide-forming agent such as phosphorus pentachloride is added. The reaction mixture is stirred in the cold for from 1 to 3 hours.

The cold reaction mixture is then treated with an alcohol such as a $C_1$-$C_4$ alkanol, benzyl alcohol or, preferably, a glycol such as propylene glycol or 1,3-butanediol. The temperature of the reaction mixture is then raised to about −5° C. to about 5° C. The product precipitates, is filtered, washed with methylene chloride and dried.

During the N-deacylation any reactive substituent groups of the substituted quinolinium group ($R_1$ and $R_2$) are protected from reaction with the imino halide-forming reagent. For example, an amino group or carboxy substituent is protected. Since the 7-amino nucleus compound is used in the preparation of compounds of the invention wherein R is an acyl group via the above-described acylation, the protected substituent group is preferably left intact to likewise protect the substituent group during the subsequent N-acylation.

The compounds of the formula 1 wherein R is formyl are useful intermediates for preparing the antibiotic compounds of this invention. They can be used in a method for preparing the 7-amino-3-(substituted quinolinium-1-ylmethyl)-3-cephem-4-carboxylate nucleus compounds (formula 1, R=H) which is a useful alternative to the side chain N-deacylation method described above.

According to this alternative method, N-formyl 7-aminocephalosporanic acid (7-formamidocephalosporanic acid) is converted to the silylated 3-iodomethyl derivative 7-formamido-3-iodomethyl-3-cephem-4-carboxylic acid silyl ester by the method of Bonjouklian described hereinabove. The 3-iodomethyl derivative is reacted with the substituted quinoline to obtain a compound represented by the formula 1 wherein R is formyl. The N-formyl product is converted to the 7-amino nucleus compound (formula 1, R=H) by hydrolysis in methanolic hydrochloric acid.

The compounds of the invention wherein R is an acyl group can be prepared by another alternative procedure comprising the displacement of the acetoxy group of the desired 7-acylamino-3-acetoxymethyl cephalosporin with the substituted quinoline. The reaction is illustrated as follows.

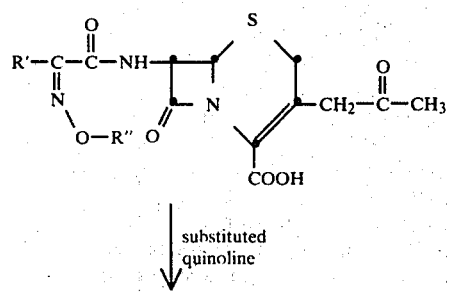

substituted quinoline

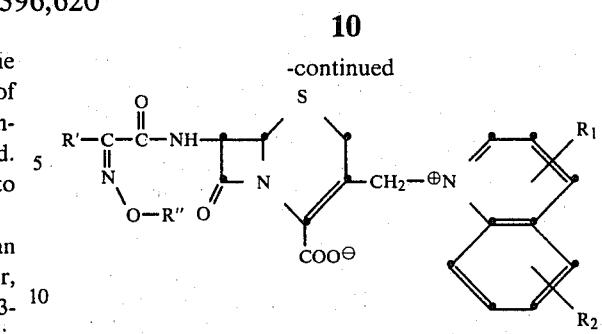

The reaction is carried out in an aqueous solvent system of water and a water miscible organic solvent such as acetone, DMF, DMAC or other suitable solvent at a temperature between about 20° C. and about 55° C. A small amount of an alkali metal iodide such as sodium iodide may be added to the reaction mixture to enhance the reaction rate and yield of the reaction.

The 7-[2-(heterocyclic)-2-oximinoacetamido]-3-acetoxymethyl-3-cephem-4-carboxylic acids, represented by the above formula 2, which are used to prepare the compounds of the invention are known or can be prepared as described herein. Heymes, et al., U.S. Pat. No. 4,152,432 describe the compound of formula 2 wherein R' is 2-aminothiazol-4-yl and R" is lower alkyl; the compounds wherein R' is 2-aminopyridin-6-yl, 2-aminopyrimidin-5-yl, or 4-aminopyrimidin-2-yl, are described by U.S. Pat. No. 4,267,176; the compounds of the formula 2 wherein R' is 5-amino-1,2,4-thiadiazol-3-yl are described by European Patent Application No. 0,007,470; and the compounds of formula 2 wherein R' is 3-aminopyrazol-5-yl or pyrazol-5-yl are prepared as described by UK Patent Application No. 2,046,734A.

The compounds of the formula 2 are prepared by acylating 7-aminocephalosporanic acid as illustrated by the following reaction scheme.

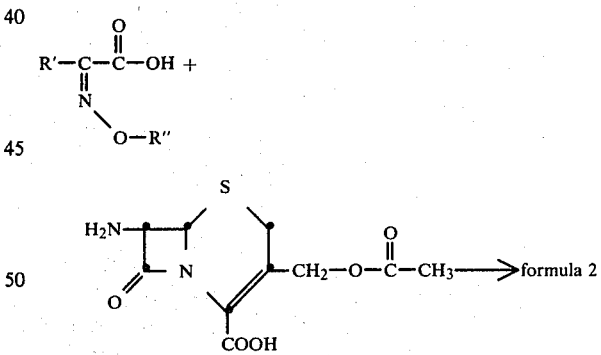

The acylation is preferably carried out with an active derivative of the oximino-substituted acid, for example with an acid halide, acid azide, or an ester. Active esters formed with ethyl chloroformate or isobutyl chloroformate, or with hydroxybenzotriazole (HBT) are suitable in the acylation. The acylation can be carried out in an aqueous or a non-aqueous medium. In a non-aqueous medium an ester of 7-ACA is used in a solvent such as a halogenated hydrocarbon eg., methylene chloride or chloroform, or other suitable solvent such as acetonitrile or tetrahydrofuran. Alternatively, a suspension of 7-ACA in a suitable aprotic solvent can be converted to a soluble silyl ester such as a trialkylsilyl ester and the ester acylated under non-aqueous condition.

Aqueous acylations can be carried out in water-miscible organic solvents containing water, eg., acetone-water, tetrahydrofuran-water, and the like. For example, an acid halide of the acid moiety can be used to acylate 7-ACA in the presence of a base such as sodium carbonate, sodium bicarbonate, or a tertiary amine such as triethylamine or pyridine.

The compounds of the formula 1 wherein R' is a pyrazol-5-yl or 3-aminopyrazol-5-yl group are prepared by employing methods known in the art. The 2-(pyrazol-5-yl)-2-oximinoacetic acid or the 2-(3-aminopyrazol-5-yl)-2-oximinoacetic acid is prepared and converted to an active derivative of the carboxylic acid, for example, an active ester. The active ester is coupled, via N-acylation, with 7-aminocephalosporanic acid and the 7-[2-(pyrazol-5-yl)-2-oximinoacetamido]-3-acetoxymethyl-3-cephem-4-carboxylic acid and 7-[2-(3-aminopyrazol-5-yl)-2-oximinoacetamido]-3-acetoxymethyl-3-cephem-4-carboxylic acid are converted to the corresponding 3-iodomethyl silylated derivatives as described herein. The latter are reacted with the substituted quinoline to provide a compound of the invention.

The pyrazole and aminopyrazole oximino substituted acetic acids are prepared by employing synthetic methods known in the art. For example, the 2-(pyrazol-5-yl)-2-alkoxyiminoacetic acid is prepared by heating in an inert hydrocarbon solvent the acetyl oximino compound of the formula A

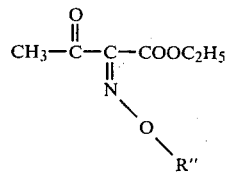   A wherein R" is other than hydrogen as defined above, with dimethylformamide dimethylacetal to form the dimethylaminomethylene oximino ester of the formula

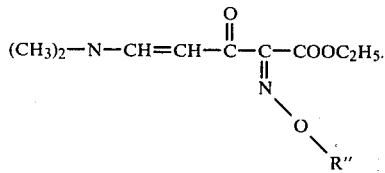

The latter is reacted with hydrazine hydrate to provide the ethyl ester of 2-(pyrazol-5-yl)-2-alkoxyiminoacetic acid. The ester is hydrolyzed to the free acid and the acid converted to an active ester for acylation.

The 2-(3-aminopyrazol-5-yl)-2-alkoxyiminoacetic acid is prepared by reacting the compound of the formula A with carbon disulfide and two equivalents of methyl iodide to form the intermediate compound of the formula B

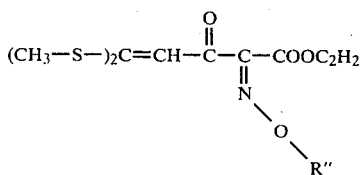   B

Intermediate B is reacted with N-t-BOC hydrazine to provide compound C,

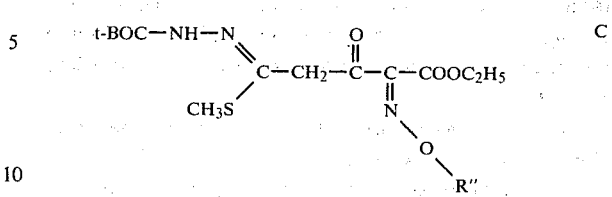   C and C is reacted with hydrazine hydrate to form 2-(3-t-BOC-hydrazinopyrazol-5-yl)-2-oximinoacetic acid ethyl ester D.

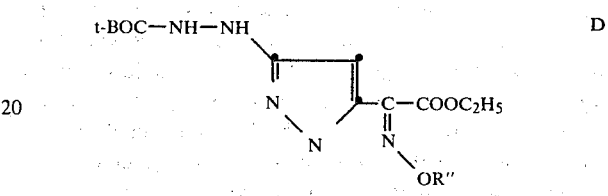   D

Compound D is treated in the cold with trifluoroacetic acid to remove the t-BOC group and the 3-hydrazinopyrazole is nitrosated with nitrous (HNO$_2$) acid in the cold to form 2-(3-azidopyrazol-5-yl)-2-oximinoacetic acid ethyl ester. The azido group is reduced to the amino group by chemical reduction to provide the 2-(3-aminopyrazol-5-yl)oximinoacetic acid ethyl ester. The ester is hydrolyzed under alkaline conditions to the free acid.

The compounds of the invention represented by the formula 1 have the normal stereochemistry of the known cephalosporin antibiotics. The 7-position side chain has the β-configuration (6R, 7R). The oximino group of the side chain can be in either the syn or anti form or as a mixture of both forms. Both the syn and anti forms of the compounds and the salts thereof possess broad spectrum antibacterial activity; however, the syn-form exhibits greater activity than the anti form and is the preferred form of the compounds of the invention. The compounds of the invention are obtained in the syn form by carrying out the acylation of 7-ACA or the 3'-substituted quinolinium nucleus (formula 1, R is H) with the syn form of the 2-(aminoheterocyclic)-2-oximinoacetic acid acylating moiety. For purposes of the acylation, the amino group of the heterocyclic ring in the 7-position side chain may be protected as described hereinabove.

The compounds of the invention, by virtue of the amino-substituted 5- or 6-membered heterocyclic ring in the 7-position side chain, form acid addition salts. Also, the compounds of the invention wherein R" is a carboxy-substituted alkyl or carboxy-substituted cycloalkyl group form salts of the carboxylic acid group. Such salts as the alkali metal salts, for example, the sodium salt, potassium salt, and the like, are useful pharmaceutically acceptable salts which can be used in formulating the antibiotics for use in treating infections. Acid addition salts formed with the amino group bonded to the heterocyclic ring in the side chain are formed with hydrochloric acid, hydrobromic acid, sulfuric acid, or phosphoric acid. Such acid addition salts are also useful pharmaceutically acceptable antibiotic salts. It will be appreciated that an amino or carboxy substituent group of the substituted quinolinium group in the 3'-position also can be converted to the salt form.

Salts can be formed with strong acids such as hydrochloric acid wherein the $C_4$ carboxylate anion is acidified to the carboxylic acid and the anion of the quinolinium cation is the anion of the strong acid, e.g. chloride in the case of hydrochloric acid. Generally, acids of greater acidity than the $C_4$ carboxylic acid will form such salts.

A preferred group of substituted quinolinium antibiotics are represented by the formula 1 wherein either $R_1$ or $R_2$ is amino and the other is hydrogen, $C_1$–$C_4$ alkyl, halogen, or $C_1$–$C_4$ alkoxy. Of these compounds the amino-substituted quinolinium compounds, wherein R' is 2-aminothiazol-4-yl, R" is $C_1$–$C_4$ alkyl, and either $R_1$ or $R_2$ is amino and the other is hydrogen are preferred. Examples of these compounds are syn-7-[2-(2-aminothiazol-4-yl)-2-methoxyiminoacetamido]-3-(5-aminoquinolinium-1-ylmethyl)-3-cephem-4-carboxylate, syn-7-[2-(2-aminothiazol-4-yl)-2-methoxyiminoacetamido]-3-(3-aminoquinolinium-1-ylmethyl)-3-cephem-4-carboxylate, and syn-7-[2-(2-aminothiazol-4-yl)-2-methoxyiminoacetamido]-3-(7-aminoquinolinium-1-ylmethyl)-3-cephem-4-carboxylate.

Another preferred group of antibiotics are represented by the formula 1 wherein either $R_1$ and $R_2$ is carbamoyl and the other is hydrogen, $C_1$–$C_4$ alkyl, halogen, or $C_1$–$C_4$ alkoxy. The mono-carbamoyl-substituted quinolinium compounds of this group are preferred.

A further preferred group of compounds of the invention are represented by the formula 1 wherein either of $R_1$ and $R_2$ are hydroxy, and the other is hydrogen, hydroxy, $C_1$–$C_4$ alkyl, $C_1$–$C_4$ alkoxy, or halogen.

The compounds of the formula 1 wherein R is an acyl group as defined herein and the pharmaceutically acceptable non-toxic salts thereof possess valuable broad spectrum antibacterial properties. These compounds are effective in inhibiting the growth of gram-negative microorganisms pathogenic to man and animals such as pseudomonas, hemophilus, proteus, enterobacter, shigella, salmonella and other genera. They also inhibit the growth of the gram-positive microorganisms such as the staphylococci, including methicillin resistant staphylococci, and streptococci.

The antibiotic compounds represented by the formula 1 wherein R is an acyl group and the pharmaceutically acceptable non-toxic salts thereof can be formulated into pharmaceutical compositions suitable for use in the treatment of infectious diseases in man and animals. According to a further aspect of this invention, there are provided antibiotic formulations comprising an antibiotic compound of the formula 1 and a pharmaceutically acceptable carrier. Formulations for parenteral administration comprise the antibiotic or a salt thereof at a suitable concentration in a diluent such as Water-For-Injection, 5% dextrose, 0.9% saline, Ringer's solution, or other physiologically compatible diluent. The concentration in the diluent can vary depending upon the mode of parenteral administration. For intramuscular administration the concentration of the antibiotic in general can be between about 0.1 g./ml. to about 1 g./ml. For intravenous administration the antibiotic or a salt thereof is formulated in a physiological fluid, such as one of those described above, and the formulation administered by the i.v. drip method.

The antibiotics also can be formulated in dosage unit form comprising between about 100 mg. and 2 g. of the dry antibiotic in solid form in sterile capped vials or sterile hermetically-sealed ampoules. In such forms the antibiotic may be in amorphous or crystalline form and may be mixed with a buffer, desiccant, or blending agent. Such dosage unit formulations are suitable for storage and shipment of the antibiotic and, as with other antibiotics, upon dissolution in the desired diluent in the vial or ampoule the solution is withdrawn by syringe and injected.

This invention also provides a method for treating bacterial infections in mammals which comprises administering in a dose of between about 100 mg. to about 2.0 g. of a compound of the formula 1, wherein R is an acyl group, or a pharmaceutically acceptable non-toxic salt thereof.

The antibiotic may be administered intramuscularly, subcutaneously, or intravenously in a single dose or in multiple doses during the day. When administered i.v. the infusion method is conveniently employed. For example, a dosage unit formulation of the antibiotic is mixed with a physiological fluid such as 5% dextrose and administered by infusion.

In practicing the method of this invention the particular dosage and the total number of doses administered will depend on such factors as the nature of the infection, its severity, the age and general health of the patient, as well as the tolerance of the individual to the antibiotic.

The following examples further illustrate the invention. The abbreviations used in the examples have the following meanings: HPLC is high performance liquid chromatography; NMR is nuclear magnetic resonance spectrum, while the letters characterizing the signals in the spectra have the following meanings: s is singlet, d is doublet, m is multiplet, q is quartet, and bs is broad singlet; DMSOd6 is deuterated dimethylsulfoxide; MSTFA is N-methyl-N-trimethylsilyltrifluoroacetamide; TMSI is trimethylsilyliodide; THF is tetrahydrofuran.

The NMR spectra were run on a Joel model No. FX-90.

The following compounds can be prepared by following the procedures and utilizing the reaction conditions and reagents described herein. In the examples, R', R", R''', $R_1$ and $R_2$ refer to the formula 1.

| Example No. | R' | R" | $R_1$ | $R_2$ |
|---|---|---|---|---|
| 1 | 2-AT | $CH_3$ | 4-$NH_2$ | H |
| 2 | " | $C_2H_5$ | H | 5-$NH_2$ |
| 3 | " | —$CH_2COOH$ | 3-Cl | 5-OH |
| 4 | " | —$C(CH_3)_2COOH$ | 4-$CONH_2$ | H |
| 5 | " | —$C(CH_3)_2COOH$ | 3-Cl | 5-$CONH_2$ |
| 6 | 2-ATD | $CH_3$ | 4-OH | H |
| 7 | " | $CH_3$ | 4-$NH_2$ | 6-Cl |
| 8 | " | $CH_3$ | 3-Cl | 5-Cl |
| 9 | " | i-$C_3H_7$ | H | 5-$COOCH_3$ |
| 10 | " | —$C(CH_3)CH_2COOH$ | 3-CN | H |
| 11 | " | —$C(CH_3)_2COOH$ | 4-$NH_2$ | H |
| 12 | 2-APyr | OH | 3-$COCH_3$ | H |
| 13 | " | $CH_3$ | 4-$NH_2$ | 7-COOH |
| 14 | " | $CH_3$ | 4-OH | 6-$CH_3$ |
| 15 | " | —$CH_2COOH$ | 3-$CH_3$ | 5-$CH_3$ |
| 16 | " | $CH_3$ | 4-OH | 7-OH |
| 17 | 4-APyr | OH | H | 8-OH |
| 18 | " | OH | 3-$C_2H_5$ | 6-OH |
| 19 | " | $CH_3$ | 4-$CF_3$ | H |
| 20 | " | —$C(CH_3)_2COONa$ | 4-$CONH_2$ | 6-F |
| 21 | " | —$CONHCH_3$ | H | 5-Cl |
| 22 | 2-APy | OH | H | 8-OH |
| 23 | " | OH | 4-$CH_2OH$ | 7-Cl |

-continued

| Example No. | R'¹ | R" | R₁ | R₂ |
|---|---|---|---|---|
| 24 | " | ⌗–C–COOH (cyclobutyl) | 3-CF₃ | H |
| 25 | " | CH₃ | H | 5-SO₃H |
| 26 | " | —CH₂COOH | 4-(CH₃)N— | 8-Cl |
| 27 | 3-APz | OH | H | 8-CN |
| 28 | " | CH₃ | 3-Cl | 5-OH |
| 29 | " | —C(CH₃)₂CONH₂ | H | 7-COOH |
| 30 | " | —C(CH₃)₂COOH | 4-NH₂ | 6-C₂H₅ |
| 31 | " | i-C₄H₉ | 4-OH | 6-SO₂NH₂ |
| 32 | 5-AIT | OH | 3-Cl | 5-OH |
| 33 | " | CH₃ | 3-NH₂ | 5-NH₂ |
| 34 | " | —CH₂COOH | 4-CH₃ | 8-CHO |
| 35 | " | CH₃ | 4-CONH₂ | 8-Cl |
| 36 | " | CH₃ | 4-COCH₃ | 6-Cl |
| 37 | Py | CH₃ | 4-OH | H |
| 38 | " | CH₃ | H | 5-NH₂ |
| 39 | " | —CH₂COOC₂H₅ | 4-OH | H |
| 40 | " | —C(CH₃)₂COOH | 4-OH | 7-Cl |

¹2-AT = 2-aminothiazol-4-yl; 2-ATD is 5-amino-1,2,4-thiadiazol-3-yl; 2-APyr is 2-aminopyrimidin-5-yl; 4-APyr is 4-aminopyrimidin-2-yl; 2-APy is 2-aminopyridin-6-yl; 3-APy is 3-aminopyrazol-4-yl; 3-AIT is 3-aminoisothiazol-5-yl; Py is pyrazol-5-yl.

EXAMPLE 41 syn-7-[2-(2-Aminothiazole-4-yl)-2-methoxyiminoacetamido]-3-(5-aminoquinolinium-1-ylmethyl)-3-cephem-4-carboxylate To a suspension of 11.8 g. of syn-7-[2-(2-aminothiazol-4-yl)-2-methoxyiminoacetamido]-3-acetoxymethyl-3-cephem-4-carboxylic acid in 50 ml. of chloroform were added 16.25 ml. of N-methyl-N-trimethylsilyltrifluoroacetamide and the mixture was stirred for 1 hour to obtain complete solution. The solution was treated with 10 ml. of trimethylsilyliodide, stirred for 15 minutes, and then evaporated to dryness. The residue of the silylated 3-iodomethyl derivative was dissolved in 50 ml. of acetonitrile and 2.12 ml. of tetrahydrofuran were added to the solution.

One-thirteenth of the solution of the 3-iodomethyl cephalosporin was added to a solution of 346 mg. of 5-aminoquinoline in 2 ml. of acetonitrile containing 853 μl. of N-methyl-N-trimethylsilyltrifluoroacetamide and the mixture was stirred for 3 hours at room temperature. After 235 μl. of water were added to the reaction mixture the Title compound was filtered and dried. There were obtained 1.28 g. of the crude product which yielded 220 mg. of purified product after HPLC chromatography of the crude.

NMR (DMSOd₆): signals at 9.55–9.28 (m, 3H), 7.9 (m, 3H), 7.32–6.92 (m, 5H), 6.70 (s, 1H), 5.74 (bs, 2H), 5.60 (q, 1H), 4.99 (d, 1H), 3.77 (s, 3H), and 3.11 (q, 2H).

EXAMPLE 42 syn-7-[2-(2-Aminothiazol-4-yl)-2-methoxyiminoacetamido]-3-(3-aminoquinolinium-1-ylmethyl)-3-cephem-4-carboxylate A suspension of 910 mg. of syn-7-[2-(2-aminothiazol-4-yl)-2-methoxyiminoacetamido]-3-acetoxymethyl-3-cephem-4-carboxylic acid in 4 ml. of chloroform was treated with 1.25 ml. of N-methyl-N-trimethylsilyltrifluoroacetamide to form a solution of the abovenamed trimethylsilyl derivative. With stirring 768 μl. of trimethylsilyliodide were added by pipette and the reaction mixture was stirred at room temperature for 15 min. The reaction mixture was then evaporated to dryness, the solid residue of the silylated 3-iodomethyl derivative was dissolved in 4 ml. of acetonitrile and 163 μl. of tetrahydrofuran and the solution was stirred for 5 minutes. To the solution was added a solution of 346 mg. of 3-aminoquinoline and 853 μl. of N-methyl-N-trimethylsilyltrifluoroacetamide in 2 ml. of acetonitrile and the mixture was stirred for about 3 hours. After 235 μl. of water were added to the mixture by pipette, the precipitate containing the title compound was filtered and dried. The purified product (100 mg.) was obtained by chromatography of the precipitate by HPLC.

NMR (DMSOd6/D₂O): signals at 9.16 (bs, 1H), 8.7 (m, 1H), 8.1 (m, 2H), 7.8 (m, 2H), 6.77 (s, 1H), 5.91 (bs, 2H), 5.69 (d, 1H), 5.05 (d, 1H), 3.84 (s, 3H), and 3.20 (q, 2H).

EXAMPLE 43 syn-7-[2-(2-Aminothiazol-4-yl)-2-methoxyiminoacetamido]-3-(7-aminoquinolinium-1-ylmethyl)-3-cephem-4-carboxylate A suspension of 9.10 g. of syn-7-[2-(2-aminothiazol-4-yl)-2-methoxyiminoacetamido]-3-acetoxymethyl-3-cephem-4-carboxylic acid in 40 ml. of chloroform was silylated by adding 12.5 ml. of N-methyl-N-trimethylsilyltrifluoroacetamide to the suspension and stirring for 1.5 hours. To the solution obtained were added 7.68 ml. of trimethylsilyliodide and the mixture was stirred for 15 minutes. The reaction mixture was evaporated to dryness and the solid residue of the silylated 3-iodomethyl derivative was dissolved in 40 ml. of acetonitrile and 1.40 ml. of tetrahydrofuran. The solution was stirred for about 5 minutes.

A one-tenth aliquot of the solution of the silylated 3-iodomethyl derivative was added to a solution of 345 mg. of 7-aminoquinoline in 2 ml. of acetonitrile containing 853 μl. of N-methyl-N-trimethylsilyltrifluoroacetamide and the mixture was stirred at room temperature for 3 hours. After 235 μl. of water were added by pipette, the impure title compound was separated by filtration and dried. There were obtained 1.15 g. of the product. The product was purified by HPLC and 106 mg. of the purified product were obtained.

NMR (DMSOd6/D₂O): signals at 8.84 (d, 1H), 8.63 (d, 1H), 8.16–7.82 (m, 1H), 7.72-6.92 (m, 3H), 6.70 (s, 1H), 5.62 (d, 1H), 5.51 (bs, 2H), 4.97 (d, 1H), 3.77 (s, 3H), and 3.07 (q, 2H).

EXAMPLE 44 syn-7-[2-(2-Aminothiazol-4-yl)-2-methoxyiminoacetamido]-3-(4-carbamoylquinolinium-1-ylmethyl)-3-cephem-4-carboxylate By following the procedures and conditions described by Example 41, 4-carbamoylquinoline is reacted with syn-7-[2-(2-aminothiazol-4-yl)-2-methoxyiminoacetamido]-3-iodomethyl-3-cephem-4-carboxylic acid trimethylsilylated derivative to form the title compound.

EXAMPLE 45 syn-7-[2-(2-Aminothiazol-4-yl)-2-methoxyiminoacetamido]-3-(4-thiocarbamoylquinolinium-1-ylmethyl)-3-cephem-4-carboxylate The title compound is prepared by reacting 4-thiocarbamoylquinoline with the silylated 3-iodomethyl derivative by following the procedures and by using the solvents and conditions described by Example 43.

EXAMPLE 46 syn-7-[2-(2-Aminothiazol-4-yl)-2-methoxyiminoacetamido]-3-(5-trifluoromethylquinolinium-1-ylmethyl)-3-cephem-4-carboxylate syn-7-[2-(2-Aminothiazol-4-yl)-2-methoxyiminoacetamido]-3-acetoxymethyl-3-cephem-4-carboxylic acid is silylated and the silylated derivative allowed to react with trimethylsilyliodide by following the procedures and conditions described by the above examples. The silylated 3-iodomethyl derivative is then reacted with 5-trifluoromethylquinoline providing the title compound.

EXAMPLE 47 syn-7-[2-(2-Aminothiazol-4-yl)-2-methoxyiminoacetamido]-3-(5-hydroxyquinolinium-1-ylmethyl)-3-cephem-4-carboxylate To a suspension of 910 mg (2 mmole) of syn-7-[2-(2-aminothiazol-4-yl)-2-methoxyiminoacetamido]-3-acetoxymethyl-3-cephem-4-carboxylic acid in 5 ml. of methylene chloride were added 1.24 ml. (7 mmole) of MSTFA, and the suspension was warmed to 40° C. until a complete solution was obtained. The solution was cooled to room temperature and 0.77 ml. (5.4 mmole) of TMSI were added. The reaction mixture was stirred for one hour under nitrogen and was then evaporated. The silylated 3-iodomethyl derivative, obtained as an oil, was dissolved in 10 ml. of acetonitrile and 0.16 ml. (2 mmole) of THF were added to the solution by pipette. After a solution was stirred at room temperature for about 15 minutes, a solution of 348 mg. (2.4 mmole) of 5-hydroxyquinoline in 10 ml. of acetonitrile (obtained silylating a suspension of the quinoline in acetonitrile with MSTFA) was added. The reaction mixture was stirred at room temperature under nitrogen for 3.5 hours, was diluted with diethyl ether and four drops of water. The heavy brown precipitate was stirred for 15 minutes sonnicated, filtered, washed with diethyl ether and dried under vacuum at 40° C. for one hour. The crude product weighed 1.11 g.

The product was purified on $C_{18}$ silica reverse phase HPLC using 5% acetonitrile-2% acetic acid-93% water (percent by volume). The purification gave 50 mg. of the product as an orange solid.

NMR (DMSO): signals at 9.4 (m, 3H), 8.0 (m, 2H), 7.25 (m, 4H), 6.7 (s, 1H), 5.9 (s, 2H), 5.7 (q, 1H), 5.1 (d, 1H), 3.75 (s, 3H), and 3.2 (d, 2H)δ.

EXAMPLE 48 syn-7-[2-(2-Aminothiazol-4-yl)-2-methoxyiminoacetamido]-3-(6-hydroxyquinolinium-1-ylmethyl)-3-cephem-4-carboxylate By following the procedures and using the reagents solvents and reaction conditions described by Example 43, 910 mg. of syn-7-[2-(2-aminothiazol-4-yl)-2-methoxyiminoacetamido]-3-acetoxymethyl-3-cephem-4-carboxylate was converted to the silylated 3-iodomethyl derivative and the latter reacted with 348 mg. of 6-hydroxyquinoline. The product was purified $C_{18}$ silica reverse phase HPLC using 10% acetonitrile-2% acetic acid-88% water which provided 289 mg. of the product as a yellow solid.

NMR (DMSOd$_6$): signals at 9.6 (d, 1H), 9.4 (d, 1H), 9.0 (t, 2H), 8.0 (m, 3H), 7.6 (s, 1H), 6.7 (s, 1H), 6.0 (s, 2H), 5.7 (q, 1H), 5.05 (d, 1H), 3.75 (s, 3H), and 3.3 (q, 2H)δ.

UV: $\lambda_{max}$ 252 nm ($\epsilon$=24,884).

Titration: $pK_a$ 3.6, 7.3, and 9.0.

EXAMPLE 49 syn-7-[2-(2-Aminothiazol-4-yl)-2-methoxyiminoacetamido]-3-(7-hydroxyquinolinium-1-ylmethyl)-3-cephem-4-carboxylate By employing the procedures, reagents, solvents, and reaction conditions described by Example 43, 910 mg. of the same starting material was converted to the silylated 3-iodomethyl derivative and the latter reacted with 348 mg. of 7-hydroxyquinoline. The product was purified by $C_{18}$ silica reverse phase HPLC using 10% acetonitrile-2% acetic acid-88% water which gave 232 mg. of the product as a yellow solid.

NMR (DMSOd$_6$): signals at 9.6 (d, 1H), 9.15 (d, 1H), 8.95 (d, 1H), 8.2 (d, 1H), 7.8 (s, 2H), 7.4 (d, 1H), 7.2 (s, 2H), 6.7 (s, 1H), 5.6 (m, 3H), 5.05 (d, 1H), 3.8 (s, 3H), and 3.35 (q, 2H)δ.

UV: $\lambda_{max}$ 254 nm ($\epsilon$=20,377).

Titration: $pK_a$ 3.9, 6.35, and 7.35.

I claim:

1. A compound of the formula

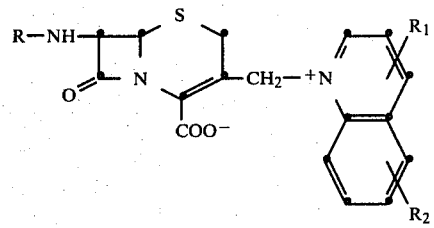

wherein R is formyl, or an acyl group of the formula

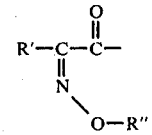

wherein R' is a 5- or 6-membered heterocyclic ring of the formulas

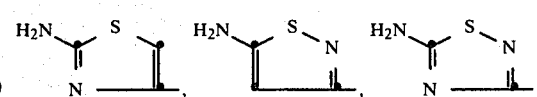

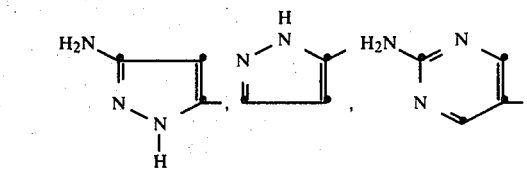

-continued

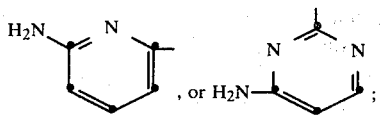

R" is $C_1$-$C_4$ alkyl, a carboxy-substituted alkyl, or carboxy-substituted cycloalkyl group of the formula

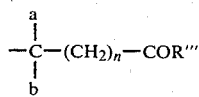

wherein n is 0-3, a and b when taken separately are independently hydrogen or $C_1$-$C_3$ alkyl, or when taken together with the carbon to which they are attached form a $C_3$-$C_7$ carbocyclic ring; R''' is hydroxy, $C_1$-$C_4$ alkoxy, amino, and when R''' is hydroxy a carboxy-protecting group; $R_1$ and $R_2$ independently are hydrogen, amino, $C_1$-$C_4$ alkylamino, di-($C_1$-$C_4$alkyl)amino, or hydroxy; provided that one of $R_1$ or $R_2$ is other than hydrogen; and the pharmaceutically acceptable, non-toxic salts thereof.

2. The compound of claim 1 wherein R is an acyl group of the formula

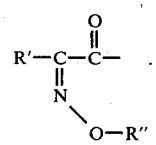

3. The compound of claim 2 wherein R" is a carboxy-substituted alkyl or cycloalkyl group of the formula

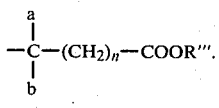

4. The compound of claim 2 wherein R" is $C_1$-$C_4$ alkyl.

5. The compound of claim 4 wherein either $R_1$ or $R_2$ is amino.

6. The compound of claim 5, said compound being syn-7-[2-(2-aminothiazol-4-yl)-2-methoxyiminoacetamido]-3-(5-aminoquinolinium-1-ylmethyl)-3-cephem-4-carboxylate.

7. The compound of claim 5, said compound being syn-7-[2-(2-aminothiazol-4-yl)-2-methoxyiminoacetamido]-3-(3-aminoquinolinium-1-ylmethyl)-3-cephem-4-carboxylate.

8. The compound of claim 5, said compound being syn-7-[2-(2-aminoquinolinium-1-ylmethyl)-2-methoxyiminoacetamido]-3-(7-aminoquinolinium-1-yl-methyl)-3-cephem-4-carboxylate.

9. The compound of claim 4 wherein either $R_1$ or $R_2$ is hydroxy.

10. The compound of claim 9, said compound being syn-7-[2-(2-aminothiazol-4-yl)-2-methoxyiminoacetamido]-3-(5-hydroxyquinolinium-1-ylmethyl)-3-cephem-4-carboxylate.

11. The compound of claim 9, said compound being syn-7-[2-(2-aminothiazol-4-yl)-2-methoxyiminoacetamido]-3-(6-hydroxyquinolinium-1-ylmethyl)-3-cephem-4-carboxylate.

12. The compound of claim 9, said compound being syn-7-[2-(2-aminothiazol-4-yl)-2-methoxyiminoacetamido]-3-(7-hydroxyquinolinium-1-ylmethyl)-3-cephem-4-carboxylate.

13. The compound of claim 1 wherein R is formyl.

14. A pharmaceutical formulation comprising a therapeutically effective amount of an antibiotic compound of claim 2 or a pharmaceutically acceptable non-toxic salt thereof wherein R is acyl and a pharmaceutically acceptable diluent.

15. The formulation of claim 14 wherein either $R_1$ or $R_2$ is amino.

16. The formulation of claim 14 wherein either $R_1$ or $R_2$ is hydroxy.

17. A method for treating bacterial infections in a mammal which comprises administering in a dose of between about 100 mg. to about 2 g. of an antibiotic compound of claim 2 or a pharmaceutically acceptable salt thereof.

18. The method of claim 17 where in the compound administered either $R_1$ or $R_2$ is amino.

19. The method of claim 17 where in the compound administered either $R_1$ or $R_2$ is hydroxy.

* * * * *